United States Patent [19]

Lund et al.

[11] Patent Number: 4,952,725

[45] Date of Patent: Aug. 28, 1990

[54] PROCESS FOR THE PREPARATION OF 4,4′DINITROSTILBENE-2,2′-DISULFONIC ACID AND ITS SALTS

[75] Inventors: Richard B. Lund, Jackson; Wesley W. McConnell, Saraland; Sam G. Ladd, Mobile, all of Ala.

[73] Assignee: Ciba-Geigy Corporation, Ardsley, N.Y.

[21] Appl. No.: 165,648

[22] Filed: Mar. 8, 1988

[51] Int. Cl.$^5$ ............................................ C07C 143/24
[52] U.S. Cl. ...................................................... 562/60
[58] Field of Search ........................ 260/505 R; 562/60

[56] References Cited

U.S. PATENT DOCUMENTS 4,719,051  1/1988  Guglielmetti .
4,734,532  3/1988  Kopp et al. .

FOREIGN PATENT DOCUMENTS 167394  12/1976  Hungary .
2136430  9/1984  United Kingdom .

OTHER PUBLICATIONS

J. Org. Chem. 32 137–146 (1967).

Primary Examiner—Alan Siegel
Attorney, Agent, or Firm—Kevin T. Mansfield

[57] ABSTRACT

The present invention relates to an improved process for the preparation of 4,4′-dinitrostilbene-2,2′-disulfonic acid and its salts.

27 Claims, No Drawings

PROCESS FOR THE PREPARATION OF 4,4'DINITROSTILBENE-2,2'-DISULFONIC ACID AND ITS SALTS

The compound 4,4'-dinitrostilbene-2,2'-disulfonic acid (DNS) is an important industrial intermediate useful in the preparation of many fluorescent dyes. Large quantities of this compound are manufactured annually. Consequently, any improvements in the process which would improve the economics by increasing the product yield and/or decreasing the effluent treatment requirements are important.

Various processes for the industrial preparation of 4,4'-dinitrostilbene-2,2'-disulfonic acid and its salts are known and comprise oxidative condensation of 2 mols of 4-nitrotoluene-2-sulfonic acid under aqueous alkaline conditions. Oxidizing agents which have been described are oxygen (air) in the presence of a catalyst or sodium hypochlorite. The numerous shortcomings of these aqueous processes have been discused in detail on pages 1 and 2 of U.S. Pat. No. 4,719,051 (Jan. 12, 1988) to Guglielmetti. For example they must be carried out at high dilution, i.e. about 5% solids, due to the heat of reaction and the poor solubility in water of the initially formed dinitrobenzyl intermediate. Additionally significant amounts of by-products are formed.

As a result of various studies on oxidative condensations of arylmethanes under alkaline conditions, the overall course of the reaction and some of the reasons for the relatively poor yields and high amounts of by-products are believed to be understood. Under alkaline conditions p-nitrotoluene-2-sulfonic acid (HPNTSA) exists in the form of its salt, e.g. NaPNTSA if sodium hydroxide is the base. In the presence of additional base, the corresponding benzyl anion can exist in equilibrium with the NaPNTSA. Under oxidizing conditions, a coupling reaction to form the sparingly soluble dinitrodibenzyl (DNDB) intermediate occurs. Further oxidation converts the DNDB to the desired DNS. Unfortunately the reaction scheme is complicated by the formation of varying amounts of intensely colored stilbene polyazo compounds. These compounds are generally of the formula

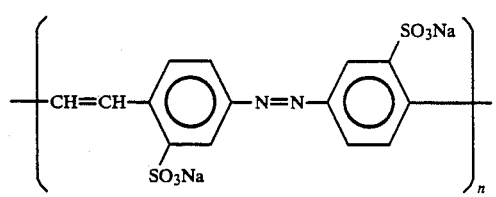

wherein n is usually from 1–6. The reaction is also complicated by the further oxidation of the DNS. If the oxidation is continued long enough to ensure reasonably complete conversion of the NaPNTSA and DNDB to DNS, then considerable amounts of oxidative DNS by-products are formed. The main chemical reactions leading to the formation and subsequent destruction of DNS can be summarized as follows.

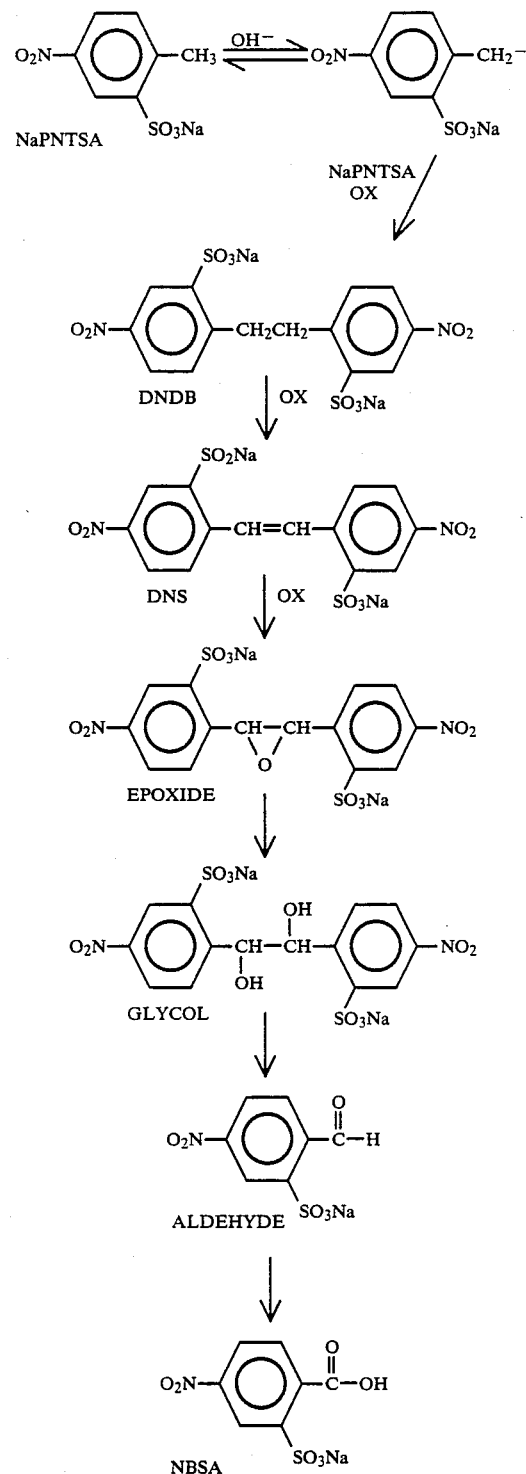

As a result of by-product formation and further oxidation during DNS synthesis, the aqueous air oxidation process only yields 4,4'-dinitrostilbene-2,2'-disulfonic acid and its salts in yields which are between about 60 and 75% (cf., for example, German Offenlegungsschrift No. 2,258,530) and is accompanied by severe effluent treatment problems.

However, it is known that nitro-, dinitro- and trinitrotoluenes can be oxidized in organic solvents, in the presence of strong bases and condensed in the presence or absence of catalysts, by oxygen (air) to give complex mixtures of products which contain corresponding nitrostilbene compounds (cf. C.A. 84, 58886 n (1976) (Kompolthy et al, Hungarian Patent application No. 167,394 published Dec. 31, 1976); Acta Chem. Scand. 25, 3509–3516 (1971); J. Org. Chem. 32, 137–46 (1967) and Advan. Chem. Ser. 51, 112–71 (1965)). Note that these products are not nitrostilbene sulfonates. Further, these oxidation reactions proceed with poor yields of nitrostilbene compounds, less than 70%, and are accompanied by the formation of considerable amounts of undesirable by-products.

Previously mentioned U.S. Pat. No. 4,719,051 to Guglielmetti discloses that 4,4'-dinitrostilbene-2,2'-disulfonic acid (DNS) and its salts can be prepared in good yields by oxidation of 4-nitrotoluene-2-sulfonic acid if the oxidation is carried out in an organic solvent. Aprotic dipolar organic solvents are generically disclosed as being suitable, with dialkylamides as exemplified by dimethylformamide being preferred. Additionally all of the examples wherein yields above 50% are obtained employ substantial amounts of methanol as a second solvent. The oxidation is carried out by gradually adding a dimethylformamide solution of an alkali metal salt of PNTSA, e.g. NaPNTSA, to a cooled dimethylformamidemethanol mixture containing a transition metal salt as catalyst, preferably manganese sulfate, and at least one equivalent of a base, preferably an alkali metal hydroxide or alkoxide, while simultaneously passing air or oxygen through the reaction mixture during the addition and subsequent several-hour hold period. Following this general procedure, yields from about 83% up to as high as 95.6% were obtained.

While the high yields make this process appear attractive relative to the aqueous processes heretofore employed, it is nevertheless not completely satisfactory from the standpoint of commercialization. While the yield based on NaPNTSA is satisfactory, relatively large amounts of two different solvents, a base and catalyst are required. One of the reasons for the large excess of the base is that dimethylformamide is partially converted to a formate salt and dimethylamine under alkaline conditions. This consumes part of the base, reduces the amount of dimethylformamide available for possible recovery and necessitates an acid scrubber to prevent pollution by the dimethylamine.

Recovery of dimethylformamide from the aqueous methanolic waste stream of the Guglielmetti process is difficult and expensive. However there is another, even more serious problem inherent in the use of dimethylformamide. It is known to be an experimental teratogen and to adversely affect the central nervous system in humans. Hence special precautions to protect female lab and plant personnel from the substance as well as air monitoring to ensure that time weighted average exposure levels are below 10 ppm (parts per million) for all workers are required. Because of the extra expenses involved in ensuring safe working conditions, use of dimethylformamide should be avoided where possible.

OBJECT OF THE INVENTION

It is an object of the present invention to develop an improved process for the preparation of 4,4'-dinitrostilbene-2,2'-disulfonic acid or its salts wherein the yield and quality are high, without resorting to the use of a hazardous solvent which requires exposure monitoring and is difficult and expensive to recover.

It is a further object of this invention to develop a process having a significantly higher throughput than the known processes by increasing the concentration of reactants and/or decreasing the reaction time.

It is a further object of this invention to develop a process wherein the recycle of the solvent can be carried out in a simple and cost-effective manner.

It is a further object of this invention to decrease the cost of treating the aqueous effluent associated with DNS manufacture by decreasing the amounts of heavy metals, highly colored materials and/or oxidative DNS by-products contained therein.

THE INVENTION

Surprisingly it has been found that the above objectives can be realized by carrying out an oxidation of 4-nitrotoluene-2-sulfonic acid as its alkali metal salt with pure oxygen or air in the presence of a catalytic amount of an alkali metal hydroxide or alkoxide and a transition metal salt in dimethylsulfoxide (DMSO) as the solvent. Advantageously the oxidation of 4-nitrotoluene-2-sulfonic acid to 4,4'-dinitrostilbene-2,2'-disulfonic acid is carried out by gradually adding a solution or dispersion of a catalytic amount of an alkali metal hydroxide or alkoxide to a solution of an alkali metal salt of 4-nitrotoluene-2-sulfonic acid in dimethylsulfoxide as solvent, in the presence of a catalytically effective amount of a transition metal organic or inorganic salt, oxide or hydroxide while continuously saturating said solution with oxygen until the oxidation is essentially complete.

Dimethysulfoxide is regarded as a much less hazardous solvent with regard to worker exposure than dimethylformamide. There are no special air monitoring requirements and normal plant operating practices to minimize exposure to chemicals provide adequate worker protection.

Unlike dimethylformamide, dimethylsulfoxide is not attacked by alkali metal hydroxides and alkoxides. Therefore virtually total recovery of the solvent is possible in principle.

While the above advantages, inherently greater safety and inertness to bases might be expected, there are a number of other advantages to using dimethylsulfoxide as the reaction medium which are unobvious. The oxidative coupling of PNTSA is carried out on a metal salt of PNTSA, not on the free acid since alkaline conditions are required for carbanion formation. The alkali metal salts of PNTSA and its intermediate dibenzyl coupling product are more soluble in dimethylsulfoxide than in dimethylformamide, so higher concentrations can be employed. Additionally the oxidation reaction proceeds more rapidly in dimethylsulfoxide and somewhat higher temperatures can be tolerated without adverse effects on quality and yield. The net effect of using a higher concentration of reactants and a shorter reaction time is that about 6 times as much DNS can be produced for a given size of reactor when dimethylsulfoxide is used as solvent rather than dimethylformamide. Compared to the very dilute aqueous processes, the increase in throughput is even more dramatic. Further advantages will become apparent from the discussion which follows.

The dimethylsulfoxide solvent used in the practice of this invention need not be anhydrous, but it is advantageous to have less than about 1.5% water by weight present in the initial reaction mixture. Amounts of water up to 40% can be tolerated if an anhydrous alcohol is used to dissolve the base. However, due to the resulting high viscosity of the reaction mass, high amounts of water are not desirable as they prevent operation in the PNTSA concentration range preferred in the practice of the present invention. Preferably the reaction mixture contains less than 0.5% water initially, especially if an aqueous solution of the alkali metal hydroxide is to be employed.

A base is necessary to neutralize the PNTSA prior to oxidation. Preferred bases are the hydroxides of lithium, sodium and potassium. Sodium hydroxide is most preferred because it is inexpensive and because the fluorescent dyes derived from DNS are normally marketed in the form of their sodium salts. Hence it is advantageous to employ only sodium compounds throughout the synthetic sequence.

In the Guglielmetti patent it was recommended to conduct the oxidation of NaPNTSA in the presence of an equivalent amount or a multiple thereof of a strong base. Typically about 1.6 molar equivalents of said strong base were used per equivalent of NaPNTSA. Because of the large amount of base required, it was necessary that said base be added in the form of an alkoxide such as sodium methoxide or as an essentially anhydrous hydroxide dissolved in methanol. If an aqueous hydroxide solution were employed in the high molar ratios of the Guglielmetti patent, the large amount of added water would have seriously disrupted the reaction and the advantages of the nonaqueous process would have been lost.

In the process of this invention it is preferred to use only catalytic quantities, i.e. 0.05–0.9 molar equivalents of strong base per equivalent of NaPNTSA. While the larger amounts of base of the prior art may be employed, there is no advantage to doing so. In fact excessive amounts of base may actually retard the reaction by decreasing the solubility of the dibenzyl intermediate. Additionally they complicate the subsequent workup, require additional acid for neutralization and, in general, add unnecessarily to the effluent load and costs with no offsetting benefit. It is preferred to use only 0.05 to 0.4 molar equivalents of base, especially 0.08 to 0.2 molar equivalents; advantageously dissolved in a $C_1$–$C_4$ alcohol. Naturally, to obtain reproducible results with such very low levels of base it is necessary to compensate for any residual acidity in the NaPNTSA, transition metal salt and dimethylsulfoxide, particularly if recycled undistilled dimethylsulfoxide is employed as the solvent.

Preferred strong bases are the alkali metal hydroxides and alkoxides, especially those of sodium.

While an anhydrous base such as finely divided solid sodium hydroxide or an alkoxide such as sodium methylate is suitable for use in the present process, because of the very small amount of base required, an anhydrous base is not required. Sodium methylate is expensive and moreover much or all of it is converted to sodium hydroxide by the residual water in the reaction mixture unless rigorous (and, in the case of dimethylsulfoxide, unnecessary) precautions are taken to exclude traces of water from said reaction mixture.

For ease of handling and cost it is advantageous to dry a dimethylsulfoxide reaction mixture to less than about 0.3% water by vacuum distillation and then to gradually add the necessary catalytic amount of sodium hydroxide to it as solid sodium hydroxide dissolved in a $C_1$–$C_4$ alcohol which may contain small amounts of water. This avoids the difficulties inherent in handling and adding small quantities of solid sodium hydroxide.

Another preferred mode of supplying the required amount of base is to dissolve 20–50% aqueous sodium hydroxide in a $C_1$–$C_4$ alcohol which is preferably anhydrous. In either case the base is in the form of an easily handled and metered alcohol solution.

Preferred alcohols are methanol, ethanol and isopropanol and mixtures thereof, with the choice of alcohol depending to a large extent on the workup method employed. If recovery of the alcohol is not desired, then methanol is the clear choice since it is the least expensive and far less of it is required to dissolve the sodium hydroxide. If recovery and recycle of the alcohol after crystallization of DNS from the reaction mixture is desired, then ethanol (including grades denatured with methanol and/or propanol such as SDA-3 or 94% reagent alcohol) or isopropanol may advantageously be used.

Preferred ratios of DMSO to the alcohols range from 50:1 for methanol to about 4:1 for isopropanol. While wet alcohols (up to about 10% water in the alcohol) may be used in the oxidative coupling, the yield is reduced and the amount of azostilbenes and other by-products is increased with increasing water content. The total water content in the initial reaction mass can approach about 1.5 wt. % without significantly affecting the final DNS yield or causing excessive amounts of by-products to form.

Since alcohols, even methanol, decrease the solubility of NaPNTSA and especially the dibenzyl intermediate in DMSO, use of excessive amounts should be avoided. In general, the minimum amount required to dissolve the base should be employed.

Another preferred mode of supplying the necessary amount of base is to dry the dimethylsulfoxide mixture to less than about 0.3% water by vacuum distillation and then to gradually add thereto a 10–50% aqueous sodium hydroxide solution. No alcohol is employed in this approach so the subsequent solvent recovery is simplified. When no alcohol is present intensive mixing is important so that a fine dispersion of the sodium hydroxide will be obtained in the dimethylsulfoxide reaction mixture. Preferably, the sodium hydroxide is added as no more than a 30% solution and most preferably as a 15–25% solution to ensure adequate dispersion. It is preferred to use 0.2 to 0.7 molar equivalents of base when no alcohol is present.

Temperatures from just above the freezing point of the reaction mixture, typically about 8° C. unless an alcohol is also added to the mixture, to about 60° C. are suitable for carrying out the reaction. Temperatures of from 10° C. to 25° C. and especially 12° C. to 20° C. are preferred. The reaction is exothermic and it is easier to dissipate the heat of reaction if the temperature is controlled at 4° C. or more above the freezing point of the reaction mixture.

Within the preferred temperature range the reaction is complete about 50–80 minutes after all the non-gaseous reactants are combined when a $C_1$–$C_4$ alcohol is used to dissolve the base. When aqueous base is employed the reaction takes 2–3 times as long to go to completion.

Suitable oxidizing agents are pure oxygen or mixtures thereof with inert gases such as nitrogen. Dry air is preferred for economic reasons. An adequate flow of oxygen (air) and intensive mixing are required to obtain high yields in a short reaction time.

The oxidation proceeds well at atmospheric pressure, but elevated pressures may be employed to increase the solubility of the oxygen reactant in the medium. Stopping the air flow brings the oxidation quickly to a halt, indicating that dissolution of oxygen in the reaction mixture is rate-controlling. This is advantageous from a safety standpoint.

Use of other oxidizing agents such as hydrogen peroxide, anhydrous hypochlorites or quinones is not recommended due to potential further oxidation of the DNS and/or the solvent, dimethylsulfoxide.

The oxidative coupling with air or gaseous oxygen requires a transition metal catalyst to proceed at reasonable rates. Suitable catalysts are the inorganic salts, oxides or hydroxides of transition metals and/or transition metal organic compounds or complexes, for example, those of Co, Mn, Cr, Ce, Fe, Ni, Cu, Ru, Pd, Pt or Ir (See Homogenous Catalysis of Metal Complexes, Vol. I Chapter 2: Activation of molecular oxygen, pg. 79; Academic Press N.Y. and London, 1974). Important catalysts are the inorganic and organic salts of copper and iron such as $CuSO_4.5H_2O$ and $FeSO_4.7H_2O$. However use of copper compounds should be avoided on ecological grounds where there are viable alternatives, and the use of iron compounds under basic conditions can result in filtration problems. Preferred catalysts are the salts, oxides, or hydroxides, anhydrous or hydrated, of manganese, and/or the manganese-organic compounds; such as manganese sulfate, hydroxide or the acetates. The most preferred catalyst is $Mn(OAc)_2.4H_2O$.

The amount of catalyst can vary within wide limits from trace quantities to amounts in the range of 0.1 to 10 percent by weight based on the 4-nitrotoluene-2-sulfonic acid reactant. Preferably 0.3 to 1% by weight is employed.

The starting material, 4-nitrotoluene-2-sulfonic acid (HPNTSA), is prepared by processes known per se by sulfonation of 4-nitrotoluene with oleum, for example with 25% oleum. The reaction is terminated by dilution of the sulfonation reaction mass with water or preferably by an aqueous $Na_2SO_4$ solution. It is a feature of the present invention that this crude storage-stable HPNTSA solution, which typically contains 32-36% HPNTSA, small amounts of various by-products and 3-6% sulfuric acid, can be used without further purification to prepare NaPNTSA.

DETAILED DESCRIPTION

A. Preparation of NaPNTSA

The conversion of 4-nitrotoluene-2-sulfonic acid (HPNTSA) to its sodium salt (NaPNTSA) is essentially a neutralization of the sulfonic arid group. However it must be conducted with care to avoid conditions which lead to formation of intensely colored polyazostilbenes.

The preferred neutralization reactants are $Na_2CO_3$ and NaOH. Use of $Na_2CO_3$ avoids polyazo formation but, due to foaming during neutralization, caused by $CO_2$ evolution and/or crystallization of reactants from solution, it requires excessive reaction times. Use of concentrated NaOH solutions at high temperatures has a tendency to give polyazostilbene by-products.

Aqueous NaOH of up to 50 wt. % concentration can be used to neutralize 10-30 wt. % aqueous solutions of crude $HPNTSA/H_2SO_4$ without polyazostilbene formation provided that the pH is kept below 7 and that slow NaOH addition with intensive mixing is employed to avoid localized high caustic concentrations. Advantageously the temperature is maintained at above 60° C. to avoid excessive crystallization during neutralization.

Most of the neutralized sodium p-nitrotoluene sulfonic acid (NaPNTSA) separates from the by-product $Na_2SO_4$ by crystallization on cooling. The $Na_2SO_4$ present after neutralization is advantageous as it greatly reduces the solubility of NaPNTSA. The solubility of NaPNTSA in water alone is about 13 wt. % at 26° C. With 12 or 20% of $Na_2SO_4$ in the water the solubility of NaPNTSA at 26° C. drops to 1.0 or 0.3 wt. % respectively. By recycling a portion of the filtrate to subsequent neutralizations, a concentration of 20 wt. % $Na_2SO_4$ can be maintained after neutralization and isolation. Additionally, since the recycled filtrate also contains some dissolved NaPNTSA, recycling said filtrate further reduces the NaPNTSA losses.

Isolation of the crystallized NaPNTSA by filtration removes most of the water. After filtration, the wetcake can either be vacuum dried at temperatures of about 60° C. to remove the remaining water or preferably it can be combined with fresh or recycled dimethylsulfoxide and subjected to vacuum distillation to remove the remaining water. Vacuum distillation of large quantities of water from dimethylsulfoxide is expensive. However, by first removing the majority of the undesired water from the NaPNTSA by a simple filtration, the cost of drying by vacuum distillation is greatly reduced.

Most of the $Na_2SO_4$ in the NaPNTSA wetcake is removed by a subsequent filtration of the dried dimethylsulfoxide solution. As the solubility of NaPNTSA in dimethylsulfoxide is about 41 wt. % at 26° C., no solubility problems are encountered during the drying operation.

B. Oxidation of NaPNTSA

When a dried, filtered dimethylsulfoxide solution of NaPNTSA is gradually added to a reaction medium consisting of dimethylsulfoxide, a transition metal catalyst, a base and, optionally, a minor amount of a $C_1$-$C_4$ alcohol, while simultaneously passing air through the mixture, that is, following the order of addition of reactants of the Guglielmetti patent, yields of 90-95% are obtainable. However when one proceeds in the opposite order and adds the base, dissolved in water or a minor amount of a $C_1$-$C_4$ alcohol, to the reaction medium which consists of dimethylsulfoxide, NaPNTSA and the transition metal catalyst while simultaneously passing air through the mixture, a small but reproducible 3-5% yield increase to 96-98% is achieved. Hence this order of addition is preferred.

The solution of the alkali metal hydroxide in water or in a $C_1$-$C_4$ alcohol is advantageously added to the cooled, vigorously agitated oxygenated reaction mixture over 5-45 minutes, preferably 10-20 minutes and most preferably about 15 minutes. Mixing for an additional 50-80 minutes, preferably 60-70 minutes, while continuing to pass oxygen (air) through the mixture at an adequate rate suffices to complete the reaction. The reaction is then terminated by neutralizing the excess base, for example with concentrated sulfuric acid or 20-25% oleum.

C. DNS Isolation

The DNS can be isolated from the reaction mixture as the disodium salt in various ways. Because of the very high purity and yield, it is possible to simply strip off all the dimethylsulfoxide, water (and alcohol), for example in an agitated vacuum rotary dryer at about 200° C. to obtain a high quality DNS.

Another approach is to crystallize DNS from the dimethylsulfoxide solution by adding an aqueous brine solution thereto. In a preferred variant of this approach the water, optional alcohol and 50-85% of the dimethylsulfoxide are removed by distillation. The DNS is then precipitated from the concentrated solution by addition of water and/or brine.

Alternatively DNS can be recovered from the dimethylsulfoxide reaction mixture by adding a large amount of an organic compound in which DNS is virtually insoluble. Aromatic compounds such as toluene are suitable. Advantageously alcohols, especially the alcohols used to dissolve the base can be used. Preferably ethanol, including the various grades denatured with methanol and/or isopropanol is used as the alcohol. Generally 2 to 3 times the dimethylsulfoxide charge of the second compound ensures high recovery of the DNS.

The solid product can be separated from the liquid by methods known per se, such as filtering or centrifuging.

A special advantage of using a manganese salt, especially $Mn(OAc)_2.4H_2O$ as the transition metal catalyst in combination with ethanol as the precipitation solvent is that about 90% of the manganese remains in solution for recycle into subsequent batches. Thus in one particularly preferred embodiment, DNS is precipitated from the reaction mixture after neutralization by addition of ethanol and separated by filtration. The filtrate, which still contains some DNS and by-products is then used to dissolve NaPNTSA wetcake. The ethanol azeotrope and water are then removed by vacuum distillation and the subsequent oxidation is carried out but using only 10% of the normal $Mn(OAc)_2.4H_2O$ charge.

Because of the high yield and the ability to recycle the solvents, effluent treatment requirements are far lower than in the processes of the prior art.

The examples which follow illustrate the invention. As they illustrate variations and general ranges, no restrictions to such ranges may be implied. Percentages are by weight unless indicated otherwise.

EXAMPLE 1

NaPNTSA preparation using $Na_2CO_3$

Into a 1 l. Erlenmeyer flask is charged 480 g. of $H_2O$ and 48 g. of $Na_2CO_3$. The mixture is heated to 70° C. and a crude HPNTSA solution is added while maintaining the temperature above 70° C., at a controlled rate so as to avoid excessive foaming. The addition of the crude HPNTSA solution (ca. 34% HPNTSA) is continued until the reaction mass has a pH of 8. The stirred reaction mixture is cooled to ambient temperature and then vacuum filtered. The filtrate is then refiltered. The combined filter cakes are then dried for 48 hours at 60° C. at 250 mm. vacuum. White $NaPNTSA.H_2O$ with an assay of 80–82% as dry HPNTSA is obtained in 86% yield. Additional product is recoverable by filtrate recycle.

Instead of drying, the wetcake can be dissolved in DMSO as in Example 2.

EXAMPLE 2

NaPNTSA preparation using NaOH

To a 1 l., baffled, 5 neck reactor equipped with heating mantle, thermometer, condenser with Claisen adaptor and variable speed agitator, is charged 516.7 g. of recycled NaPNTSA filtrate or a 21% $Na_2SO_4$ solution. After the mixture is heated to 90° C., 33.7 g. $Na_2SO_4$ is added to it. When the $Na_2SO_4$ has dissolved and the reaction mass has been heated to 95° C., the addition of 250 g. of crude HPNTSA solution (ca. 34% HPNTSA) is started dropwise from a 250 ml. pressure equalizing dropping funnel, maintaining the temperature above 95° C. throughout the addition. After the HPNTSA solution is charged, 25% NaOH (approximately 120 g.) is added until the pH is between 3.6–6.0 (50% NaOH can also be used if the $H_2O/Na_2SO_4$ volume is correspondingly adjusted). The heating mantle is removed and the reaction mass is allowed to cool with stirring. Crystallization of the NaPNTSA begins at 85°–90° C. After the reaction mass has cooled to 40°–45° C., an ice bath is used to cool it further to 20°–27° C. After a 30 minute hold at 20°–27° C. the slurry is filtered on a 15 cm. Buchner funnel using #541 Whatman filter paper. Vacuum is maintained for 1 hour after the liquid is removed. The yield is 99.8% based on the HPNTSA charged.

The NaPNTSA/DMSO solution used in the following examples is prepared by dissolving the NaPNTSA wetcake in DMSO and vacuum distilling at 36 mm. Hg to remove $H_2O$. When the temperature stabilizes, a water content of <0.3% is reached. Alternatively the wetcake can be dried as in Example 1.

EXAMPLE 3

The quantity of 672.56 g. of a dried NaPNTSA/DMSO mixture, prepared according to Example 2, containing 0.544 mol of NaPNTSA is charged to a 1 l. cylindrical, baffled, jacketed reaction flask equipped with bottom outlet and 5 neck reaction flask cover. To this mixture, 0.392 g. (0.0016 mol) of $Mn(OAc)_2.4H_2O$ catalyst is added, and the mixture is stirred with a mechanical stirrer (700–750 RPM) having a 4-blade non-pitched impeller until the solids are dissolved. The reaction mixture is saturated with air by sparging below the impeller continuously with dried compressed air at a flow rate of 900–1000 ml./min. The mixture is cooled to 15° C. using a Haake Model A81 refrigeration bath. Then 47.8 ml. (0.068 mol, 0.125 molar equivalents based on NaPNTSA) of 5.7% NaOH in aqueous reagent alcohol (83.7% ethanol, 4.4% methanol, 4.9% 2-propanol, 6.9% $H_2O$) is charged via a Metrohm Model 655 Dosimat automatic titrator equipped with a Dosimat Model 659 timer over 13.5 minutes while maintaining the temperature at 15°–18° C. and the air flow rate at 900–1000 ml./min. After 70 minutes the reaction mass is neutralized with 2.8 g. of 98% $H_2SO_4$. An equivalent amount of 20% oleum can be used. The yield of the DNS by high pressure liquid chromatography (HPLC) analysis is 96.9%.

EXAMPLE 4

Example 3 is repeated, except that 653.2 g. of an NaPNTSA/DMSO mixture containing 0.465 mol of NaPNTSA is charged to the reaction flask with 2.7 g. (0.011 mol) of $Mn(OAc)_2.4H_2O$ catalyst. The air flow is set at 900 ml./min. and the mixture is stirred at 735 RPM. After the reaction mass is cooled to 10° C., 52.5 g. (0.074 mol, 0.158 molar equivalents based on NaPNTSA) of 5.6% NaOH in aqueous reagent alcohol is charged over 45 minutes while maintaining the air flow and temperature conditions. After a 65 minute reaction period, the yield of DNS by HPLC is 98.0%.

EXAMPLES 5-8

These examples illustrate the effect of varying amounts of manganese acetate on yield.

Example 3 is repeated except that 653.0 g. of an NaPNTSA/DMSO mixture containing 0.431 mol of NaPNTSA is charged to the reaction vessel with the tabulated amounts of $Mn(OAc)_2.4H_2O$ catalyst. The air flow is kept constant at 800-840 ml./min. In all cases the reaction mass is cooled to 10°-12° C. before the addition of 52.5 ml. (0.063 mole, 0.145 molar equivalents based on NaPNTSA) of 5.6% NaOH in aqueous reagent alcohol which is charged over 15 minutes. The catalyst amounts, reaction times and yields by HPLC are as follows:

| Ex. No. | Catalyst | (g., mol) | Reaction Time (min.) | % Yield DNS |
|---------|----------|-----------|----------------------|-------------|
| 5 | 0.68 | (0.0028) | 51 | 95.9 |
| 6 | 0.32 | (0.0013) | 54 | 97.5 |
| 7 | 0.17 | (0.0007) | 53 | 95.5 |
| 8 | 0.08 | (0.0003) | 60 | 87.9 |

EXAMPLE 9

The reaction vessel and apparatus is exactly the same as in Example 3. To the reaction vessel the following is added: 66.5 g. (0.253 mol) of NaPNTSA, 1.6 g. (0.0065 mol) of $Mn(OAc)_2.4H_2O$ catalyst and 300.0 g. of dry DMSO. This mixture is stirred at 720 RPM until the solids have dissolved. The solution is saturated with air, sparged below the impeller at 550 ml./min. After the reaction mass has been cooled to 11° C., 99 ml. (0.035 mol, 0.137 molar equivalents based on NaPNTSA) of 1.8% NaOH in anhydrous 2-propanol is charged over 30 minutes. The yield of DNS after 20 minutes is 95.6% by HPLC.

EXAMPLE 10

Example 3 is repeated, except that 651.8 g. of an NaPNTSA/DMSO mixture containing 0.444 mol of NaPNTSA is charged to the reaction vessel with 1.8 g. (0.0072 mol) of ground $CuSO_4.5H_2O$ as catalyst. The air flow rate is set at 930 ml./min. After the mixture is cooled to 10° C., 52.5 ml. (0.059 mol, 0.133 molar equivalents based on NaPNTSA of 5.3% NaOH in reagent alcohol is charged over 32 minutes. The yield of DNS after 70 minutes by HPLC is 95.4%.

EXAMPLE 11

Example 3 is repeated except that 623.4 g. of an NaPNTSA/DMSO solution containing 0.436 mol of NaPNTSA is charged to the reaction vessel with 2.7 g. (0.0108 mol) of $CuSO_4.5H_2O$ as catalyst. The air flow is set at 900 ml./min. and the reaction mass is stirred at 750 RPM while it is cooled to 12° C. Then 173.4 ml. (0.061 mol, 0.139 molar equivalents based on NaPNTSA) of 1.8% NaOH dissolved in anhydrous 2-propanol is added to the reaction mass over 30 minutes. The DNS yield by HPLC is 91.08% after completion of 50 minutes reaction time.

Examples 12-17 illustrate that the invention can be practiced with more than a catalytic amount of base.

EXAMPLE 12

To a 1 l. cylindrical reaction flask equipped with a bottom outlet and 5 neck reaction flask cover, is added 60.1 g. (0.227 mol) of NaPNTSA, 320.0 g. of DMSO and 1.5 g. (0.006 mol) of $CuSO_4.5H_2O$ catalyst. The reaction mixture is stirred with a mechanical stirrer equipped with a 4-blade non-pitched impeller at 715 RPM and saturated with compressed air sparged below the impeller at 550 ml./min. The solution is cooled to 14° C. with an ice bath. Then 10 g. (0.25 mol, 1.10 molar equivalents based on NaPNTSA) of NaOH which has been dissolved in 70.0 g. of methanol is added dropwise over 30 minutes from a 125 ml. pressure-equalizing dropping funnel. The temperature of the reaction mass is maintained below 15° C. throughout the reaction period. After 60 minutes the DNS yield by HPLC is 95.6%.

EXAMPLE 13

Example 12 is repeated except that 65.0 g. (0.246 mol of NaPNTSA), 319.6 g. of DMSO and 1.1 g. (0.0065 mol) of $MnSO_4.H_2O$ catalyst is charged to the reaction vessel. After the mixture is cooled to 14° C., 11 g. (0.275 mol, 1.12 molar equivalents based on NaPNTSA) of NaOH dissolved in 70 g. of methanol is added over 30 minutes. After a further 90 minutes at 14° C. the yield of DNS by HPLC is 85.8%.

EXAMPLE 14

Example 12 is repeated except that 65.0 g. (0.246 mol) of NaPNTSA, 319.7 g. of DMSO and 1.7 g. (0.0061 mol) of $FeSO_4.7H_2O$ catalyst is charged to the reaction vessel. After cooling the mixture to 16° C., 11 g. (0.275 mol, 1.12 molar equivalents based on NaPNTSA) of NaOH dissolved in 71.1 g. of methanol is added over 30 minutes. After 60 minutes the yield of DNS by HPLC is 90.9%.

EXAMPLE 15

Example 12 is repeated except that 69.4 g. (0.262 mol) of NaPNTSA, 320.0 g. of DMSO and 1.5 g. (0.0061 mol) of $Mn(OAc)_2.4H_2O$ catalyst is charged to the reaction vessel. After the vigorously stirred mixture is cooled to 13° C., 11.0 g. (0.275 mol, 1.05 molar equivalents based on NaPNTSA) of NaOH dissolved in 70 g. of methanol is added over 45 minutes. After 75 minutes the yield of DNS by HPLC is 95.4%.

EXAMPLE 16

To a 1 l. jacketed flask equipped as in Example 3 is added 153.8 g. of DMSO, 10.0 g. (0.25 mol, 1.40 molar equivalents based on NaPNTSA) of NaOH, 1.5 g. (0.0060 mol) of $CuSO_4.5H_2O$ catalyst, 5.5 g. of $H_2O$ and 2.5 g. of TBMAC (tributylmethylammonium chloride). The air flow to the reactor is 70-80 ml./min. The reaction mass is heated to 60° C. before the addition of 244.4 g. of an NaPNTSA/DMSO solution containing 0.179 mol of NaPNTSA, which is added dropwise from a 500 ml. pressure-equalizing funnel over 15 minutes. After 65 minutes the yield of DNS by HPLC is 74%.

EXAMPLE 17

This example illustrates that the reaction does not proceed as well in the absence of some water and/or $C_1$-$C_4$ alcohol.

Example 3 is repeated except that 619.4 g. of an NaPNTSA/DMSO mixture containing 0.528 mol of NaPNTSA is charged to the reactor with 0.38 g. (0.0016 mol) of $Mn(OAc)_2.4H_2O$ catalyst. The air flow to the reactor is 900-920 ml./min. The mixture is stirred at 750 RPM and cooled to 12° C. Then 57.1 g. (0.139 mol, 0.26 molar equivalents based on NaPNTSA) of an NaOH/DMSO mixture, prepared by mixing 15.08 g. of NaOH and 140.0 g. of DMSO in a Waring blender, is charged over 5 minutes. After 90 minutes the yield of DNS by HPLC is only 84.9%.

EXAMPLE 18

Example 3 is repeated except that 550.5 g. of an NaPNTSA/DMSO mixture containing 0.469 mol of NaPNTSA is charged to the reaction vessel with 0.33 g. (0.0013 mol) of $Mn(OAc)_2.4H_2O$ catalyst. The air flow to the reactor is 1000 ml./min. The mixture is stirred at 1000 RPM and cooled to 20° C. after the solids have dissolved. Then 3.32 ml. (5.05 g., 0.063 mol, 0.135 molar equivalents based on NaPNTSA) of 50% NaOH is charged over 30 minutes, maintaining the reaction temperature below 20° C. The yield of DNS after 90 minutes by HPLC is only 88.2% due to incomplete dispersion of the base in the reaction mixture (see next example).

EXAMPLE 19

Example 18 is repeated except that 672.2 g. of an NaPNTSA/DMSO mixture containing 0.553 mol of NaPNTSA is charged to the reaction flask with 0.38 g. (0.0016 mol) of $Mn(OAc)_2.4H_2O$ catalyst. The air flow to the reactor is 990 ml./min. The mixture is stirred at 1000–1040 RPM and cooled to 17° C. Then 3.78 ml. (5.75 g, 0.072 mol, 0.13 molar equivalents based on NaPNTSA) of 50% NaOH dissolved in 5.0 g of methanol is charged to the reactor over 25 minutes. The yield of DNS after 70 minutes by HPLC is 94.1%.

EXAMPLES 20–24

Example 3 is repeated except that 655.0 g of a NaPNTSA/DMSO solution containing 0.478 mol of NaPNTSA is charged to the reaction flask with 1.0 g (0.0041 mol) of $Mn(OAc)_2.4H_2O$ catalyst and 28.5 g of $H_2O$. The air flow is set at 1000 ml/min. and the mixture is stirred at 800 RPM. After the reaction mass is cooled to 13° C., a solution of 11.4 g (0.143 mol, 0.298 molar equivalents based on NaPNTSA) of 50% aqueous NaOH dissolved in various quantities of methanol (MeOH) is charged over 20 min. while maintaining the air flow and agitation rates and controlling the temperature at 15°–18° C. The reactions are followed by HPLC and the time of maximum in-reactor yield determined. The following table lists the reaction times, MeOH quantities used, and DNS in-reactor yields as determinedly HPLC.

| Ex. No. | MeOH (g) | Reaction Time (min.) | % Yield DNS |
| --- | --- | --- | --- |
| 20 | 40 | 60 | 96.1 |
| 21 | 30 | 60 | 94.9 |
| 22 | 20 | 90 | 93.2 |
| 23 | 10 | 90 | 91.7 |
| 24 | 0 | 90 | 90.1 |

EXAMPLES 25–26

Example 3 is repeated except that 657.0 g of a NaPNTSA/DMSO solution containing 0.478 mol of NaPNTSA is charged to the reaction flask with 1.0 g of $Mn(OAc)_2.4H_2O$ catalyst and various quantities of $H_2O$. The air flow is set at 1000 ml/min. and the mixture is stirred at 800 RPM. After the reaction mass is cooled to 13° C., a solution of 5.7 g (0.143 mol, 0.3 molar equivalents based on NaPNTSA) of NaOH dissolved in 40.0 g. of anhydrous reagent alcohol is charged over 20 minutes while maintaining the air flow and agitation, and controlling the temperature at 15°–18° C. The reactions are followed by HPLC and the time of maximum in-reactor yield is determined. The following table lists the results obtained.

| Ex. No. | $H_2O$ (g) | Reaction Time (min.) | % Yield DNS |
| --- | --- | --- | --- |
| 25 | 28.8 | 60–90 | 96.2 |
| 26 | 61.3 | 90–120 | 97.4 |

EXAMPLE 27

The procedure of examples 25–26 is followed but with 655.7 g of a NaPNTSA/DMSO solution containing 0.477 mol of NaPNTSA and 135 g of added water. After 265 minutes a maximum yield of 89.5% by HPLC is obtained.

EXAMPLE 28

This example illustrates carrying out the oxidation in the absence of a $C_1$–$C_4$ alcohol.

Example 3 is repeated except that 688.9 g of a NaPNTSA/DMSO mixture containing 0.549 mol of NaPNTSA is charged to the reaction flask with 0.84 g (0.0041 mol) of $Mn(OAC)_2.4H_2O$ catalyst. The air flow is then set at 1000 ml./minute and the mixture is stirred at 800 RPM. After the reaction mass is cooled to 12° C., 43.6 g (0.218 mol, 0.4 molar equivalents based on NaPNTSA) of 20% aqueous NaOH is charged over 20 minutes while maintaining the temperature at 15°–19° C. After a 120 minute reaction period, the yield of DNS by HPLC is 94.5%.

EXAMPLE 29

Example 3 is repeated except that 611.7 g. of an NaPNTSA/DMSO mixture containing 0.436 mol of NaPNTSA is charged to the reaction flask. The DMSO used to prepare this mixture was previously used consecutively in six reactions and reclaimed by removing excess alcohol and water by vacuum distillation. The recycled DMSO contained 2.3% DNS, dissolved impurities and $Mn(OAc)_2.4H_2O$ catalyst (90% of the required charge) from the previous reactions. To this mixture 0.038 g. of fresh $Mn(OAc)_2.4H_2O$ is added and the air sparge is set at 900 ml./min. After the vigorously stirred reaction mass is cooled to 12° C., 45.4 g. (0.064 mol, 0.146 molar equivalents based on NaPNTSA) of 5.6% NaOH in aqueous reagent alcohol is charged over 20 minutes. After a reaction time of 60 minutes the yield of DNS, corrected for the DNS in the initial DMSO solution, is 95% by HPLC. The isolated yield, following the procedure of Example 32, is 95.6%.

EXAMPLE 30

The reaction mass (723.7 g.) from Example 3 is transferred to a 6-neck, jacketed, 2 l. crystallizer flask equipped with a bottom outlet, a thermometer, a combination pH electrode, and a mechanical stirrer fitted with a 4-blade non-pitched impeller. The reaction mass is neutralized by dropwise addition over 10 minutes of 2.8 g. of 98% $H_2SO_4$ (or an equivalent amount of 23% oleum) with mild agitation (300 RPM) while maintaining a temperature below 25° C. The pH of the solution, which is determined by combining 4.3 g. of distilled $H_2O$ with 2.0 g. of the neutralized reaction mass, is about 6.5. Then 507.9 g. of 94% reagent alcohol is charged to the vessel over 2-4 minutes. After the mixture has been stirred for 60 minutes at ambient temperature, it is cooled to 5° C. via a refrigeration bath, and stirred for a further 20 minutes. The resultant slurry is vacuum filtered utilizing a glass Buchner funnel fitted with a sintered glass disc to give 956.0 g. of filtrate. The wetcake is then washed with 300.0 g. of chilled (5° C.) 94% reagent alcohol yielding 320.5 g. of filtrate and 225.0 g. of DNS wetcake containing about 55% DNS. The isolated yield is 83% of DNS. About 12% of the DNS formed is present in the filtrates and virtually all of it can be recovered by recycle of the solvents.

EXAMPLE 31

A reaction mass (461.7 g.) is neutralized as in Example 30. After neutralization, 732 g. of toluene is added over 5 minutes to the reactor to precipitate the DNS. The wetcake is collected by vacuum filtration using a Buchner funnel with Whatman No. 1 filter paper and is dried under vacuum (250 mm. Hg) at 75° C. for 7 hours. The isolated dry yield is 83.6% DNS from a reaction mixture which had been found to have an 88.5% yield of DNS by HPLC analysis.

EXAMPLE 32

To a 1 l. reaction flask equipped as in Example 12 is added 69.4 g. (0.262 mol) of NaPNTSA, 320 g. of dimethylsulfoxide, 20.6 g. of $Na_2SO_4$ and 1.5 g. (0.0061 mol) of $Mn(OAc)_2.4H_2O$. The reaction mixture is stirred at 700 RPM and saturated with air sparged subsurface at 550 ml./min. while it is cooled to 14° C. Then 11.0 g. (0.275 moles; 1.05 molar equivalents based on NaPNTSA) of NaOH dissolved in 70 g. of methanol is added over 40 minutes. After 80 minutes at 14° C., the reaction mass is neutralized with 16.2 g. of 23% oleum. The neutralized reaction mass (505.5 g.) is charged to a 1 l. round-bottom flask equipped with a mechnical stirrer, a reflux condenser and a thermometer. The stirred reaction mixture is heated to 45° C. Then an aqueous solution of 40.6 g. NaCl in 300 g. $H_2O$ is charged to the mixture. The temperature is increased to 75°-80° C. over 10 minutes. The stirred mixture is then cooled to 10° C. with an ice bath over 50 minutes. The resultant slurry is vacuum filtered by using a Buchner funnel and Whatman No. 2 filter paper. The isolated yield is 77.7% whereas the yield by HPLC is 86.7%.

EXAMPLE 33

The reaction mass (471.9 g.) from Example 14 is neutralized as in Example 32 and is dried in a vacuum oven (74 mm. Hg) at 200° C. for 24 hours. The mass is periodically removed and ground to release the entrained solvent from the DNS crystals. The dried crude product has an assay of 88.5% as DNS with no evidence of decomposition. The major contaminant is $Na_2SO_4$ and its water of hydration.

EXAMPLE 34

Example 3 is repeated, except that 672.2 g. of an NaPNTSA/DMSO mixture containing 0.55 mol of NaPNTSA is charged to the reaction flask with 0.394 g. (0.0016 mol) of $Mn(OAc)_2.4H_2O$. The air flow is set at 900-950 ml./min. and the mixture is stirred at 710-740 RPM. After the reaction mass is cooled to 10°-12° C., 51.32 g. (0.076 mol, 0.138 molar equivalents based on NaPNTSA) of 5.9% NaOH in aqueous SD 3A alcohol (88.1% ethanol, 4.6% methanol, and 7.3% water) is charged over 25 minutes while maintaining the air flow and temperature. After a 65-75 minute reaction period, the yield of DNS by HPLC is 95.38%.

The reaction mass (722.68 g.) is treated in the same manner as in Example 30 except that 539.08 g. of aqueous SD 3A alcohol is charged to the vessel over 2-4 minutes after the reaction mass has been neutralized. After the mixture has been stirred for 10 minutes at ambient temperature, it is cooled to 5° C. via a refrigeration bath, and stirred for a further 15 minutes. The resultant slurry is vacuum filtered utilizing a glass Büchner funnel fitted with a sintered glass disk to give 1043.2 g. of filtrate. The wetcake (177.9 g.; 50.24% DNS) is then reslurried with 444.75 g. of aqueous SD 3A alcohol and heated at reflux for 30 minutes. After being cooled to ambient temperature, the slurry is further cooled to 5° C. using an ice/brine bath. Vacuum filtration utilizing a filter as described above yields 186.2 g. of wetcake at 50.79 weight percent DNS (79.78% isolated DNS yield) and 405.5 g. of filtrate.

The filtrate contains about 16% of the DNS yield. By recycling the solvent as illustrated in the next experiment, this DNS can be recovered essentially quantitatively.

EXAMPLES 35-40

Example 3 is repeated except that six consecutive reactions are performed using recycled dimethylsulfoxide from the previous reaction, along with fresh dimethylsulfoxide as needed to replace the small amount lost during water and alcohol stripping. A total of 540 g of fresh and recycled dimethylsulfoxide is used in each reaction. The dimethylsulfoxide is reclaimed as in Example 30 and contains DNS, dissolved impurities and $Mn(OAC)_2.4H_2O$ catalyst. About 0.04 g of additional $Mn(OAC)_2.4H_2O$ is added to each reaction to replace that lost.

The $Mn(OAC)_2.4H_2O$ and NaPNTSA are stirred in the dimethylsulfoxide mixture at 710-750 RPM. the resulting solution is cooled to 12° C. and the air flow is set at 900-950 ml./minute. then NaOH which is dissolved in 48-56 g of aqeuous SD 3A alcohol is charged over 23-27 minutes. After the reaction is complete the reaction mass is neutralized with 2.8-3.7 g of 98% $H_2SO_4$. The DNS is isolated as in Example 34. The charges and yields for the six reactions using recycled dimethylsulfoxide are listed in the following table. The amounts of $Mn(OAC)_2.4H_2O$ include both that present in the recycled dimethylsulfoxide (about 90%, determined by atomic absorption spectroscopy) and the additional amount, about 10%, need to compensate for the physical losses.

| Ex. No. | NaPNTSA (mol) | NaOH (mol) | $Mn(OAC)_2 4H_2O$ (g.) | $Mn(OAC)_2 4H_2O$ (mol) | Yield (HPLC) | Yield (isolated) | Time (min) |
| --- | --- | --- | --- | --- | --- | --- | --- |
| 35 | 0.535 | 0.072 | 0.3936 | 0.0016 | 98.2 | 92.1 | 60 |
| 36 | 0.558 | 0.085 | 0.4080 | 0.0017 | 95.0 | 95.5 | 83 |
| 37 | 0.581 | 0.103 | 0.3421 | 0.0014 | 95.0 | 95.8 | 100 |
| 38 | 0.540 | 0.094 | 0.4051 | 0.0017 | 95.2 | 101.8 | 125 |

-continued

| Ex. No. | NaPNTSA (mol) | NaOH (mol) | Mn(OAC)$_2$4H$_2$O) (g.) | (mol) | Yield (HPLC) | Yield (isolated) | Time (min) |
| --- | --- | --- | --- | --- | --- | --- | --- |
| 39 | 0.529 | 0.088 | ca.0.4 | ca.0.0017 | 93.6 | 102.1 | 154 |
| 40 | 0.489 | 0.088 | 0.3691 | 0.0015 | 95.4 | 97.9 | 145 |

EXAMPLE 41

A reaction mass produced as in Example 3 is vacuum distilled in a rotary evaporator at 100° C. and 6 mm. to remove the H$_2$O, alcohol and about 80% of the DMSO. The resulting slurry contains approximately 50% DMSO and 50% DNS. This slurry is crystallized twice as described below to recover the entrained DMSO and to isolate the DNS wetcake. The yield loss of DNS is kept to a low amount, 1.0% of theory, by recycling the filtrate (ML2) and wash liquor (WW) from the second crystallization.

The slurry (214.4 g) is added to a 5-necked, 1 liter round-bottomed flask equipped with a bottom outlet and an agitator with a teflon paddle blade. The slurry is dissolved by addition of 351.9 g the filtrate from the second crystallization (ML-2) of a previous experiment, then heating to 95° C. with external heating and slow agitation. When the DNS is dissolved, 30.0 g of NaCl is added to induce crystallization. After five minutes at 95° C., the stirred crystallization mass is cooled to 5° C. with an ice bath. When 5° C. is reached the mass is held at 5° C. for 5 minutes before filtration. The mass is then vacuum filtered using polypropylene filter cloth for about 5 minutes.

The 354.0 g of filtrate from the first crystallization (ML-1) is distilled to recover the remaining 20% of DMSO. The wetcake (WC-1), 239.7 g, is added to a 1 liter round-bottomed flask and dissolved by the addition of 360.6 g of wash liquor (WW) recovered from the water wash of a wetcake from the second crystallization of a previous experiment (WC-2). The wetcake (WC-1) is dissolved by heating to 85° C. with external heating and slow agitation. The stirred mass is cooled to 5° C. with an ice bath and vacuum filtered using polypropylene filter cloth. The filtration is complete in about 2 minutes. The filtrate (ML-2), 351.9 g, can be used for subsequent crystallizations of the crude 50% DNS slurry. The wetcake (WC-2) from the second crystallization is then washed with 295 g of cool (5° C.) water. After addition of the wash water, the cake is vacuum filtered and sucked dry for a total of about 5.0 minutes. The wash liquor, 360.6 g, is used for the second crystallization of a subsequent experiment. In an extended series of recycle experiments, the final wetcake has a weight of approximately 161 g with an assay of 61.7% DNS. This corresponds to an isolated yield of 94% from a reaction mixture having a 95% yield by HPLC.

What we claim is:

1. A process for the oxidation of 4-nitrotoluene-2-sulfonic acid to 4,4'-dinitrostilbene-2,2'-disulfonic acid which comprises gradually adding a solution or dispersion of 0.05 to 0.9 equivalents of an alkali metal hydroxide or alkoxide to a solution of an alkali metal salt of 4-nitrotoluene-2-sulfonic acid in dimethylsulfoxide as solvent, in the presence of a catalytically effective amount of a transition metal organic or inorganic salt, oxide or hydroxide while continuously saturating said solution with oxygen until the oxidation is essentially complete.

2. A process of claim 1 wherein the alkali metal hydroxide is sodium hydroxide or sodium methoxide.

3. A process of claim 2 wherein the akali metal hydroxide is sodium hydroxide.

4. A process of claim 1 wherein the alkali metal salt of 4-nitrotoluene-2-sulfonic acid is the sodium salt.

5. A process of claim 3 wherein the sodium hydroxide is added as a solution in water, a C$_1$-C$_4$ alcohol or a mixture thereof.

6. A process of claim 5 wherein the sodium hydroxide is dissolved in a C$_1$-C$_4$ alcohol selected from methanol, ethanol and isopropanol.

7. A process of claim 5 wherein the sodium hydroxide is added as a 10-50% aqueous solution.

8. A process of claim 1 wherein 0.08 to 0.2 molar equivalents of alkali metal hydroxide or alkoxide is used.

9. A process of claim 1 wherein the transition metal catalyst is selected from inorganic and organic salts of manganese, copper and iron.

10. A process of claim 9 wherein the catalyst is selected from inorganic and organic salts of manganese.

11. A process of claim 9 wherein the catalyst is Mn(OAc)$_2$.4H$_2$O.

12. A process of claim 1 wherein the oxidation is run at elevated pressure.

13. A process of claim 1 wherein the oxidation is carried out at a temperature between 8° and 60° C.

14. A process of claim 13 wherein the oxidation is carried out between 10° and 25° C.

15. A process of claim 13 wherein the oxidation is carried out between 12° and 20° C.

16. A process of claim 1 wherein the alkali metal hydroxide or alkoxide is neutralized 50-80 minutes after all the non-gaseous reactants are combined.

17. A process of claim 1 wherein the alkali metal hydroxide or alkoxide solution is gradually added over 5-40 minutes.

18. A process of claim 17 wherein a sodium hydroxide solution is added over 10-20 minutes.

19. A process of claim 17 wherein an aqueous sodium hydroxide solution in a C$_1$-C$_4$ alcohol is added over 5-40 minutes.

20. A process of claim 1 wherein the oxygen source is dry air.

21. A process of claim 6 wherein a solution of sodium hydroxide in an alcohol selected from methanol, ethanol and isopropanol is added to the oxygen-saturated mixture of reactants, said mixture of reactants being at a temperature of between 10° and 25° C., and neutralizing the sodium hydroxide 50-80 minutes after all the non-gaseous reactants are combined.

22. A process of claim 6 wherein the dimethylsulfoxide employed is the filtrate from a previous preparation of 4,4'-dinitrostilbene 2,2'-disulfonic acid from which water and alcohol have been removed by vacuum distillation.

23. A process of claim 21 wherein, after the sodium hydroxide has been neutralized, the water, alcohol and solvent are removed by vacuum distillation.

24. A process of claim 21 which comprises the further steps of adding a liquid in which the product is poorly soluble and separating the precipitated product from the solvent mixture.

25. A process of claim 21 wherein the liquid in which the product is poorly soluble is ethanol or toluene.

26. A process of claim 24 wherein the product is separated by vacuum filtration or centrifugation.

27. A process of claim 23 wherein, after the sodium hydroxide is neutralized, 50–85% of the dimethylsulfoxide is removed by vacuum distillation and the product is precipitated by adding an aqueous salt solution.

* * * * *